United States Patent
Yamamoto et al.

(10) Patent No.: US 10,087,128 B2
(45) Date of Patent: *Oct. 2, 2018

(54) FLUORINATED AROMATIC COMPOUND, METHOD FOR ITS PRODUCTION, CURABLE MATERIAL, ITS CURED PRODUCT, AND OPTICAL MEMBER

(71) Applicant: ASAHI GLASS COMPANY, LIMITED, Chiyoda-ku (JP)

(72) Inventors: Hiromasa Yamamoto, Chiyoda-ku (JP); Akinobu Kunimoto, Chiyoda-ku (JP); Norihide Sugiyama, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 199 days.

This patent is subject to a terminal disclaimer.

(21) Appl. No.: 15/008,136

(22) Filed: Jan. 27, 2016

(65) Prior Publication Data

US 2016/0137572 A1  May 19, 2016

Related U.S. Application Data

(63) Continuation of application No. PCT/JP2014/070491, filed on Aug. 4, 2014.

(30) Foreign Application Priority Data

Aug. 7, 2013 (JP) .................. 2013-164619

(51) Int. Cl.
| | |
|---|---|
| C07C 43/29 | (2006.01) |
| C08F 116/12 | (2006.01) |
| G02B 1/04 | (2006.01) |
| C08F 12/22 | (2006.01) |
| C08F 12/34 | (2006.01) |
| C08F 12/20 | (2006.01) |

(52) U.S. Cl.
CPC .............. *C07C 43/29* (2013.01); *C08F 12/20* (2013.01); *C08F 12/22* (2013.01); *C08F 12/34* (2013.01); *C08F 116/12* (2013.01); *G02B 1/045* (2013.01)

(58) Field of Classification Search
None
See application file for complete search history.

(56) References Cited

U.S. PATENT DOCUMENTS

| | | |
|---|---|---|
| 2004/0127632 A1 | 7/2004 | Kim et al. |
| 2004/0198906 A1 | 10/2004 | Ding et al. |
| 2008/0132669 A1 | 6/2008 | Eriguchi et al. |
| 2008/0293903 A1* | 11/2008 | Petrucci-Samija ..... C08F 12/16 526/246 |
| 2009/0215961 A1 | 8/2009 | Bongiovanni et al. |
| 2010/0172623 A1* | 7/2010 | Park ...................... C07C 43/225 385/143 |

FOREIGN PATENT DOCUMENTS

| | | |
|---|---|---|
| JP | 4-9807 | 1/1992 |
| JP | 5-507742 | 11/1993 |

(Continued)

OTHER PUBLICATIONS

Tkachenko, "Fluorinated allyl-, acetyl-, and bromo-containing hydroxyl-substituted phenyl ethers with a hexafluorobenzene or decafluorobiphenyl central unit", Journal of Fluorine Chemistry, 2013, 149, 36-41. (Year: 2013).*

(Continued)

*Primary Examiner* — Nicole M Buie-Hatcher
(74) *Attorney, Agent, or Firm* — Oblon, McClelland, Maier & Neustadt, L.L.P.

(57) ABSTRACT

To provide a novel fluorinated aromatic compound having at least two carbon-carbon unsaturated bonds, a method for its production, a curable material comprising the fluorinated aromatic compound, a cured product thereof, and an optical member. The fluorinated aromatic compound is represented by formula (A), wherein n is an integer of 0 to 6, a is an integer of 0 to 5, b is an integer of 0 to 4, c is an integer of 0 to 4, a+c+n is 2 to 6, a+b is 2 to 9, Z is a single bond, —O—, —S—, —CO—, —C(CH$_3$)$_2$—, —C(CF$_3$)$_2$—, —SO—, or —SO$_2$—, Rf$^1$ is a C$_{1-8}$ fluoroalkyl group, Y$^1$ and Y$^2$ are each independently a group represented by formula (1) (s is 0 or 1, and R$^1$, R$^2$, R$^3$, and R$^4$ are each independently a hydrogen atom or a fluorine atom), and F in the aromatic ring indicates that hydrogen atoms in the aromatic ring are all substituted by fluorine atoms.

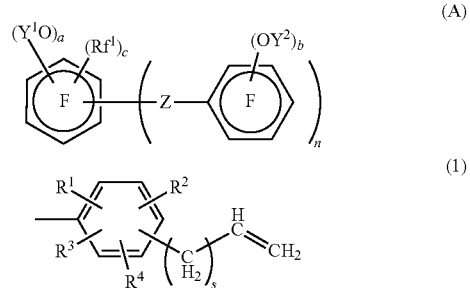

8 Claims, No Drawings

(56) References Cited

FOREIGN PATENT DOCUMENTS

| JP | 2003-171439 | 6/2003 |
|---|---|---|
| JP | 2004-186168 | 7/2004 |
| JP | 2004-300089 | 10/2004 |
| JP | 2008-539304 | 11/2008 |
| WO | WO 2006/137327 A1 | 12/2006 |

OTHER PUBLICATIONS

International Search Report dated Nov. 4, 2014 in PCT/JP2014/070491 filed Aug. 4, 2014.
J.V. Crivello, et al. "Synthesis and Photopolymerization of Monomers Bearing Isopropenylphenoxy Groups" Journal of Polymer Science: Part A: Polymer Chemistry, vol. 33, 1995, pp. 653-663.

* cited by examiner

FLUORINATED AROMATIC COMPOUND, METHOD FOR ITS PRODUCTION, CURABLE MATERIAL, ITS CURED PRODUCT, AND OPTICAL MEMBER

TECHNICAL FIELD

The present invention relates to a novel fluorinated aromatic compound, a method for its production, a curable material containing the fluorinated aromatic compound, its cured product, and an optical member comprising the cured product.

BACKGROUND ART

In the optical and electronic equipment field, transparent resins are used for optical members such as optical films, optical sheets, transparent substrates, lenses, etc. Resins used for such optical applications are broadly divided into thermoplastic resins and thermosetting resins, and as the thermoplastic resins, an acrylic resin such as polymethyl methacrylate, a polycarbonate, a cycloolefin polymer, a fluorine resin such as CYTOP (registered trademark, manufactured by Asahi Glass Company, Limited), etc. are known. As the thermosetting resins, an epoxy resin, a silicone resin, etc. are known.

In recent years, in the optical and electronic equipment field, use of high intensity laser light or blue light, or near-ultraviolet light, is spread, and a resin excellent in transparency, heat resistance and light resistance has been demanded.

In general, a thermoplastic resin is softened and flows at a high temperature, and therefore, it is not suitable for use at a significantly high temperature. On the other hand, a thermosetting resin has at least two crosslinkable functional groups, and when heated or irradiated with light, it will be cured by a reaction of the crosslinkable functional groups one another. Its cured product is less likely to flow even at a high temperature and has high heat resistance, and thus, it is suitable for use at a high temperature.

Among such thermosetting resins, an epoxy resin is excellent in heat resistance. However, a usual epoxy resin has an aromatic ring and is not sufficiently transparent in a near ultraviolet region from ultraviolet. An alicyclic epoxy resin having no aromatic ring can form a cured product excellent in transparency even in a near ultraviolet region from ultraviolet (Patent Document 1). However, the cured product is not sufficient in heat resistance and light resistance. A silicone resin can form a cured product which is excellent in transparency from a visible light range to a near ultraviolet region and excellent in light resistance and heat resistance (Patent Document 2). However, the cured product has a large thermal expansion coefficient and a large permeability of gas such as moisture and oxygen, which may cause problems in the reliability of the electronic device.

In recent years, in order to meet the demand for larger capacity and higher speed of information processing in optical communication systems and computers, optical transmission systems have come to be used. There is an optical waveguide as a basic constituting component in an optical device or the like to be used in an optical transmission system. As a resin-type optical waveguide, an optical waveguide having a fluorinated polyimide as the constituting component (Patent Document 3) is, for example, known.

However, a fluorinated polyimide is brittle, and its elastic modulus is high, so that it may undergo warpage in the production process. Further, for such a fluorinated polyimide, a special monomer is required, which is expensive and lacks in applicability to the production of general-purpose optical waveguides.

Thus, a novel compound is desired which is a curable compound having at least two crosslinkable functional groups and which is capable of producing a cured product that sufficiently satisfies characteristics required for optical members such as optical characteristics such as transparency, heat resistance, mechanical properties, etc.

PRIOR ART DOCUMENTS

Patent Documents

Patent Document 1: JP-A-2003-171439
Patent Document 2: JP-A-2004-186168
Patent Document 3: JP-A-4-9807

DISCLOSURE OF INVENTION

Technical Problem

It is an object of the present invention to provide a novel fluorinated aromatic compound having at least two carbon-carbon unsaturated bonds, a method for its production, a curable material containing the fluorinated aromatic compound, its cured product, and an optical member.

Solution to Problem

The present invention provides a fluorinated aromatic compound, a method for its production, a curable material, its cured product, and an optical member, having the following constructions [1] to [11].

[1] A fluorinated aromatic compound represented by the following formula (A).

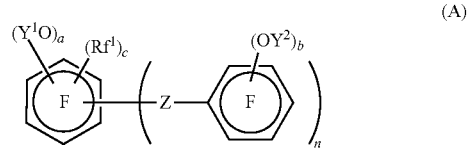

wherein n is an integer of from 0 to 6, a is an integer of from 0 to 5, b is an integer of from 0 to 4, c is an integer of from 0 to 4, a+c+n is from 2 to 6, a+b is from 2 to 9, Z is a single bond, —O—, —S—, —CO—, —C(CH$_3$)$_2$—, —C(CF$_3$)$_2$—, —SO— or —SO$_2$—, Rf$^1$ is a C$_{1-8}$ fluoroalkyl group, each of Y$^1$ and Y$^2$ which are independent of each other, is a group represented by the following formula (1), and F in the aromatic ring represents that hydrogen atoms of the aromatic ring are all substituted by fluorine atoms,

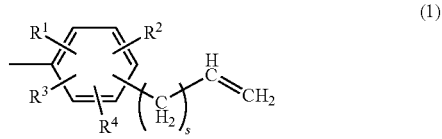

wherein s is 0 or 1, and each of R$^1$, R$^2$, R$^3$ and R$^4$ which are independent of one another, is a hydrogen atom or a fluorine atom.

[2] The fluorinated aromatic compound according to the above [1], which has a molecular weight of from 300 to 2,000.
[3] The fluorinated aromatic compound according to the above [1] or [2], which satisfies both conditions:
that each of $R^1$, $R^2$, $R^3$ and $R^4$ in $Y^1$ and $Y^2$ in the formula (A) is a hydrogen atom, and
that in the formula (A), c is 0, or c is an integer of from 1 to 4 and $Rf^1$ is a $C_{1-8}$ perfluoroalkyl group.
[4] The fluorinated aromatic compound according to the above [3], represented by the following formula (A-1) or (A-2):

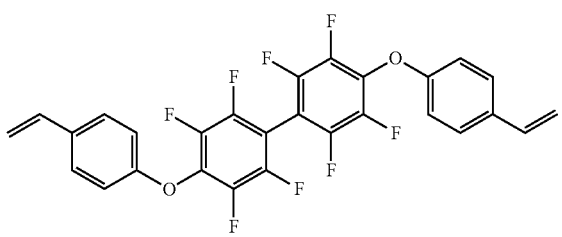 [SMILES: C=Cc1ccc(Oc2c(F)c(F)c(-c3c(F)c(F)c(Oc4ccc(C=C)cc4)c(F)c3F)c(F)c2F)cc1]
(A-1)

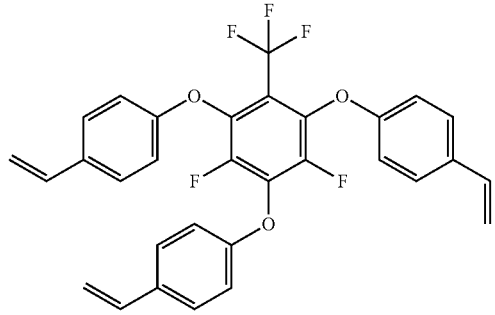
(A-2)

[5] A method for producing the fluorinated aromatic compound as defined in the above [1], which is characterized by comprising a step of subjecting an aromatic compound represented by the following formula (a1) and a fluorinated aromatic compound represented by the following formula (a2) to a condensation reaction in the presence of a HF elimination agent:

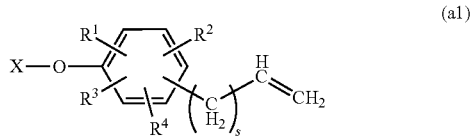
(a1)

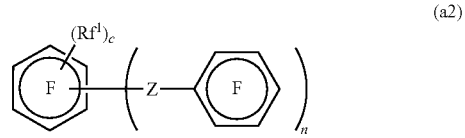
(a2)

in the formula (a1), s is 0 or 1, each of $R^1$, $R^2$, $R^3$ and $R^4$ which are independent of one another, is a hydrogen atom or a fluorine atom, and X is a hydrogen atom, $CH_3CO$, $CH_3CH_2CO$, $(CH_3)_3C(CH_3)_2Si$ or $(CH_3)_3Si$, and in the formula (a2), n is an integer of from 0 to 6, c is an integer of from 0 to 4, c+n is from 0 to 6, Z is a single bond, —O—, —S—, —CO—, —C(CH$_3$)$_2$—, —C(CF$_3$)$_2$—, —SO—, or —SO$_2$—, $Rf^1$ is a $C_{1-8}$ fluoroalkyl group, and F in the aromatic ring represents that hydrogen atoms of the aromatic ring are all substituted by fluorine atoms.
[6] The method for producing a fluorinated aromatic compound according to the above [5], wherein the aromatic compound represented by the formula (a1)) is 4-ethenyl phenol or 4-ethenyl-1-acetoxy benzene.
[7] The method for producing a fluorinated aromatic compound according to the above [5] or [6], wherein the fluorinated aromatic compound represented by the formula (a2) is perfluorobenzene, perfluorotoluene, perfluoroxylene, perfluorobiphenyl, perfluoroterphenyl, a perfluorotriphenyl benzene, a perfluorotetraphenyl benzene, a perfluoropentaphenyl benzene, a perfluorohexaphenyl benzene, a 1,1'-oxybis[2,3,4,5,6-pentafluorobenzene], a 1,1'-thiobis[2,3,4,5,6-pentafluorobenzene], a bis(2,3,4,5,6-pentafluorophenyl) methanone, a 1,1'-sulfonyl bis[2,3,4,5,6-pentafluoro benzene], or a 1,2,3,4,5-pentafluoro-6-[(2,3,4,5,6-pentafluorophenyl) sulfinyl] benzene.
[8] The method for producing a fluorinated aromatic compound according to any one of the above [5] to [7], wherein the HF elimination agent is an alkali metal hydroxide.
[9] A curable material which is characterized by containing the fluorinated aromatic compound as defined in any one of the above [1] to [4].
[10] A cured product obtained by curing the curable material as defined in the above [9].
[11] An optical member comprising the cured product as defined in the above [10].

Advantageous Effects of Invention

The fluorinated aromatic compound of the present invention is a novel compound having at least two carbon-carbon unsaturated bonds. According to the method for producing the fluorinated aromatic compound of the present invention, it is possible to produce the fluorinated aromatic compound of the present invention. According to the fluorinated aromatic compound and a curable composition containing it of the present invention, it is possible to produce a cured product. The cured product is excellent in optical characteristics such as transparency, heat resistance, mechanical properties, etc., and thus is useful as an optical member.

DESCRIPTION OF EMBODIMENTS

[Fluorinated Aromatic Compound]
The fluorinated aromatic compound of the present invention (hereinafter referred to also as the fluorinated aromatic compound (A)) is represented by the following formula (A) and has at least two carbon-carbon unsaturated bonds.

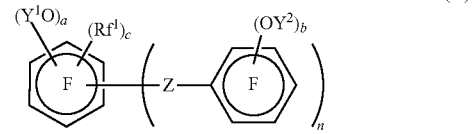
(A)

wherein n is an integer of from 0 to 6, a is an integer of from 0 to 5, b is an integer of from 0 to 4, c is an integer of from 0 to 4, a+c+n is from 2 to 6, a+b is from 2 to 9, Z is a single bond, —O—, —S—, —CO—, —C(CH$_3$)$_2$—, —C(CF$_3$)$_2$—, —SO— or —SO$_2$—, $Rf^1$ is a $C_{1-8}$ fluoroalkyl group, each of $Y^1$ and $Y^2$ which are independent of each other, is a group represented by the following formula (1), and F in the aromatic ring represents that hydrogen atoms of the aromatic ring are all substituted by fluorine atoms,

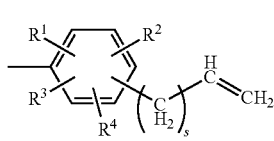
(1)

wherein s is 0 or 1, and each of $R^1$, $R^2$, $R^3$ and $R^4$ which are independent of one another, is a hydrogen atom or a fluorine atom.

In the above formula (A), n is preferably from 0 to 4, more preferably from 0 to 3.

a is preferably from 1 to 3, more preferably from 1 to 2.

b is preferably from 1 to 3, and more preferably from 1 to 2.

c is preferably 0 or 1, more preferably 0.

a+c+n is preferably from 2 to 4. a+b is preferably from 2 to 6.

Z is preferably a single bond, —O— or —S—, more preferably a single bond or —O—.

The number of carbon atoms in the fluoroalkyl group in $Rf^1$ is preferably from 1 to 6, more preferably from 1 to 4, most preferably 1. The fluoroalkyl group is preferably a perfluoroalkyl group, since it is excellent in heat resistance. Specific examples thereof include a perfluoromethyl group, a perfluoroethyl group, a perfluoropropyl group, a perfluorobutyl group, a perfluorohexyl group, a perfluorooctyl group, etc. As $Rf^1$, a perfluoromethyl group is most preferred.

Each of $Y^1$ and $Y^2$ which are independent of each other, is a group represented by the above formula (1) (hereinafter referred to also as the group (1)).

In the formula (1), s is preferably 0, from the viewpoint of excellent crosslinking reactivity.

Further, from the viewpoint of excellent crosslinking reactivity, at least one among $R^1$, $R^2$, $R^3$ and $R^4$, is preferably is a hydrogen atom, and it is particularly preferred that each of $R^1$, $R^2$, $R^3$ and $R^4$ is a hydrogen atom. Among $R^1$, $R^2$, $R^3$ and $R^4$, as the number of those which are hydrogen atoms is large, the reactivity of the group (1) becomes high, the fluorinated aromatic compound (A) or a curable material containing it will be excellent in curability, and an obtainable cured product will be excellent in heat resistance.

Specific examples of the group (1) include a vinyl-substituted phenyl group, an allyl-substituted phenyl group, etc. A vinyl-substituted phenyl group is preferred, since the crosslinking reactivity is high, and a high crosslinking density is obtainable.

In the formula (A), $Y^1$ and $Y^2$ may be the same or different and are preferably the same.

The molecular weight of the fluorinated aromatic compound (A) is preferably from 300 to 2,000, more preferably from 350 to 1,000. When the molecular weight is within this range, curing among molecules easily occurs, and it will be easy to obtain a cured product excellent in transparency, heat resistance and strength.

From the viewpoint of excellent effects of the present invention, the fluorinated aromatic compound (A) is preferably one which satisfies both conditions that each of $R^1$, $R^2$, $R^3$ and $R^4$ in $Y^1$ and $Y^2$ in the formula (A) is a hydrogen atom, and that in the formula (A), c is 0, or c is an integer of from 1 to 4 and $Rf^1$ is a $C_{1-8}$ perfluoroalkyl group, particularly preferably a compound represented by the following formula (A-1) or (A-2).

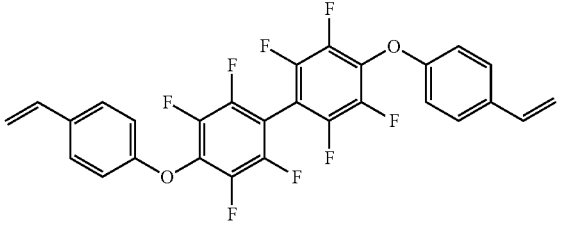
(A-1)

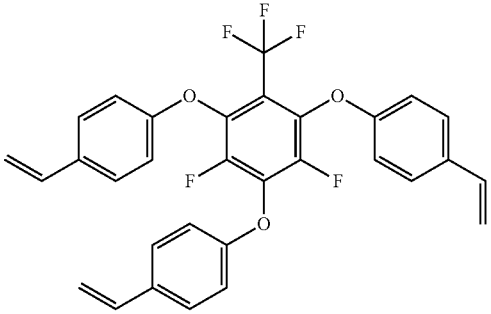 [SMILES: C=Cc1ccc(Oc2c(F)c(Oc3ccc(C=C)cc3)c(C(F)(F)F)c(Oc3ccc(C=C)cc3)c2F)cc1]
(A-2)

<Method for Producing Fluorinated Aromatic Compound (A)>

The method for producing the fluorinated aromatic compound (A) is not particularly limited, but is preferably a method of subjecting an aromatic compound represented by the following formula (a1)) (hereinafter referred to as the aromatic compound (a1)) and a fluorinated aromatic compound represented by the following formula (a2) (hereinafter referred to as the fluorinated aromatic compound (a2)) to a condensation reaction in the presence of a HF elimination agent.

In the condensation reaction, by such a reaction mechanism that phenoxy ions derived from —OX in the aromatic compound (a1)) will attack carbon atoms to which fluorine atoms in the aromatic ring in the fluorinated aromatic compound (a2) are bonded, and then the fluorine atoms will be removed, to form ether bonds, whereby the fluorinated aromatic compound (A) will be obtained.

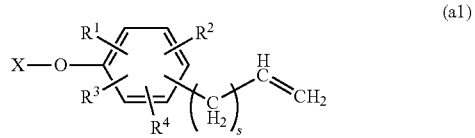
(a1)

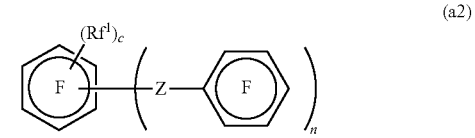
(a2)

In the formula (a1), s is 0 or 1, each of $R^1$, $R^2$, $R^3$ and $R^4$ which are independent of one another, is a hydrogen atom or a fluorine atom, and X is a hydrogen atom, $CH_3CO$, $CH_3CH_2CO$, $(CH_3)_3C(CH_3)_2Si$ or $(CH_3)_3Si$. In the formula (a2), n is an integer of from 0 to 6, c is an integer of from 0 to 4, c+n is from 0 to 6, Z is a single bond, —O—, —S—, —CO—, —C(CH_3)_2—, —C(CF_3)_2—, —SO—, or —SO$_2$—, Rf$^1$ is a C$_{1-8}$ fluoroalkyl group, and F in the aromatic ring represents that hydrogen atoms of the aromatic ring are all substituted by fluorine atoms.

The preferred ranges and more preferred ranges of s, and R$^1$, R$^2$, R$^3$ and R$^4$ in the formula (a1), are the same as those in the formula (A).

X is preferably a hydrogen atom, CH$_3$CO or CH$_3$CH$_2$CO.

Specific examples of the aromatic compound (a1)) include phenols having reactive double bonds, e.g. ethenyl phenols such as 4-ethenyl phenol (referred to also as 4-hydroxystyrene), 2-ethenyl phenol, 3-ethenyl phenol, 4-ethenyl-tetrafluorophenol, etc., 2-propenyl phenols such as 2-(2-propenyl) phenol, 3-(2-propenyl) phenol, 4-(2-propenyl) tetrafluorophenol, etc., and their derivatives such as 4-ethenyl-1-acetoxy benzene (referred to also as p-acetoxystyrene), 4-ethenyl-1-trimethylsiloxy benzene, etc. In these derivatives, in the production of the fluorinated aromatic compound (A), an acetoxy group or trimethylsiloxy group is converted to a hydroxy group (a phenolic hydroxy group), which will be reacted with a fluorinated aromatic compound (a2).

From the viewpoint of the reactivity of crosslinkable unsaturated double bonds, the aromatic compound (a1)) is more preferably an aromatic compound having an ethenyl group, further preferably an aromatic compound containing no fluorine atom, most preferably 4-ethenyl phenol or 4-ethenyl-1-acetoxy benzene.

The fluorinated aromatic compound (a2) constitutes the skeleton of the fluorinated aromatic compound (A).

The preferred ranges and more preferred ranges of n, c, Z and Rf$^1$ in the formula (a2), are the same as in the formula (A).

Specific examples of the fluorinated aromatic compound (a2) include perfluorobenzene, perfluorotoluene, perfluoroxylene, perfluorobiphenyl, perfluoroterphenyl, a perfluorotriphenyl benzene, a perfluorotetraphenyl benzene, a perfluoropentaphenyl benzene, a perfluorohexaphenyl benzene, a 1,1'-oxybis[2,3,4,5,6-pentafluorobenzene], a 1,1'-thiobis[2,3,4,5,6-pentafluorobenzene], a bis(2,3,4,5,6-pentafluorophenyl) methanone, a 1,1'-sulfonyl bis[2,3,4,5,6-pentafluorobenzene], a 1,2,3,4,5-pentafluoro-6-[(2,3,4,5,6-pentafluorophenyl) sulfinyl] benzene, etc.

From the viewpoint of easy production and availability of raw materials, the fluorinated aromatic compound (a2) is preferably perfluorobenzene, perfluorotoluene or perfluorobiphenyl. Further, from such a viewpoint that the cured product is excellent in heat resistance, perfluorotoluene or perfluorobiphenyl is more preferred.

As the HF elimination agent to be used in the production of the fluorinated aromatic compound (A), a basic compound is preferred, and a carbonate, hydrogen carbonate or hydroxide of an alkali metal is particularly preferred. Specific examples include sodium carbonate, potassium carbonate, sodium hydrogen carbonate, potassium hydrogen carbonate, sodium hydroxide, potassium hydroxide, etc. As the HF elimination agent, an alkali metal hydroxide is preferred.

In the condensation reaction of an aromatic compound (a1)) and a fluorinated aromatic compound (a2), the amount of the HF elimination agent is required to be at least 1 mol, preferably from 1.1 to 3 mol, per 1 mol of the aromatic compound (a1).

The condensation reaction is preferably carried out in a polar solvent, from the viewpoint of the solubility of the reaction reagents and the increase of the reaction rate. The polar solvent is preferably a solvent containing an aprotic polar solvent such as N,N-dimethylacetamide (hereinafter referred to as DMAc), N,N-dimethylformamide, N-methylpyrrolidone, dimethyl sulfoxide or sulfolane.

In the polar solvent, within a range not to decrease the solubility of the resulting fluorinated aromatic compound (A) and not to adversely affect the condensation reaction, toluene, xylene, benzene, tetrahydrofuran, benzotrifluoride, xylene hexafluoride, etc. may be contained. By containing these, the polarity (dielectric constant) of the solvent may be changed to control the reaction rate.

Otherwise, in a solvent other than a polar solvent, the fluorinated aromatic compound (A) can be produced by the above-described method. For example, a low polar solvent such as ethylene glycol dimethyl ether, diethylene glycol dimethyl ether (hereinafter referred to also as diglyme), triethylene glycol dimethyl ether or tetraethylene glycol dimethyl ether may be mentioned.

The condensation reaction conditions are preferably from 1 to 72 hours at from 0 to 100° C.

Particularly, in the case of conducting the condensation reaction in a polar solvent, with a view to preventing an abrupt progress of the reaction and preventing side reactions to impair formation of the desired product, from 2 to 48 hours at from 3 to 50° C. are preferred, from 9 to 24 hours at from 5 to 20° C. are more preferred, and from 12 to 24 hours at from 5 to 10° C. are particularly preferred.

In a case where the condensation reaction is carried out in a solvent other than a polar solvent, from the viewpoint of the production efficiency, the increase of the reaction rate, etc., from 12 to 24 hours at from 40 to 80° C. are particularly preferred.

After the condensation reaction of the aromatic compound (a1)) and the fluorinated aromatic compound (a2), the fluorinated aromatic compound (A) may, as the case requires, be purified by a method such as neutralization, reprecipitation, extraction, filtration or the like. Metals (potassium, sodium etc.) derived from the HF elimination agent and fluorine atoms liberated by the condensation reaction, should preferably be sufficiently purified and removed, since they are likely to degrade the performance of an optical member, such as the transparency, strength, etc.

From the viewpoint of efficiency, such purification is preferably carried out in a state where the polar solvent used during the production is present.

The structure of the obtained fluorinated aromatic compound (A) can be identified by a known analytical method, such as nuclear magnetic resonance (NMR), size exclusion chromatography (SEC) or the like.

Advantageous Effects

The fluorinated aromatic compound (A) has at least 2 (a+b) carbon-carbon unsaturated bonds derived from the group (1), whereby molecules of the fluorinated aromatic compound (A) will be reacted (addition-polymerized) with one another by heating or irradiation with light, and it is possible to obtain a cured product of the fluorinated aromatic compound (A). Moreover, the group (1) in the fluorinated aromatic compound (A) is highly reactive, and therefore, the fluorinated aromatic compound (A) can be addition-polymerized alone even without adding a radical polymerization initiator (such as a photoinitiator or thermal initiator), and reaction by-products will not be formed. Therefore, the cured product of the fluorinated aromatic compound (A) contains little impurities and is excellent in transparency and light resistance. Further, the cured product consists of a fluorinated aromatic skeleton, whereby it is excellent also in heat resistance and mechanical properties.

Therefore, the fluorinated aromatic compound (A) is useful as a curable component of a curable material for the preparation of a cured product. Particularly, it is suitably used for optical applications wherein the cured product is required to have transparency, heat resistance, light resistance and mechanical properties. Here, the curable component is meant for a compound capable of forming a cured product alone.

The fluorinated aromatic compound (A) can also be used as a crosslinking aid. For example, by blending the fluorinated aromatic compound (A) as a crosslinking agent to a fluorinated elastomer, it is possible to obtain a fluorinated elastomer composition excellent in crosslinking reactivity, and of which a crosslinked product is excellent in chemical resistance and heat resistance.

The method for crosslinking a fluorinated elastomer is known to influence the properties of the resulting crosslinked product. In particular, a perfluoroelastomer is known to be not easy to crosslink. Therefore, in order to improve the properties of crosslinked product and to improve the crosslinking reactivity, various crosslinking methods have been proposed. For example, as a method for crosslinking a perfluoroelastomer, a method of reacting a perfluoroelastomer having an iodine atom as a crosslinking site at a polymer chain terminal, with a crosslinking aid, in the presence of a peroxide, has been proposed. As the crosslinking aid, triallyl isocyanurate (e.g. U.S. Pat. No. 4,243,770, WO90/014367), or 1,6-divinyl perfluorohexane (e.g. Japanese Patent No. 5,057,657) has been proposed. However, a cross-linked product obtained by using triallyl isocyanurate, is not sufficient in heat resistance, because it has a crosslinking point of the isocyanurate ring. A crosslinked product obtained by using 1,6-divinyl perfluorohexane, is excellent in heat resistance, but is not sufficient in chemical resistance, especially in amine resistance. Whereas, according to the fluorinated aromatic compound (A), it is possible to achieve both excellent chemical resistance and heat resistance.

[Curable Material]

The curable material of the present invention contains the above-described fluorinated aromatic compound (A).

The fluorinated aromatic compound (A) contained in the curable material of the present invention may be one type, or two or more types.

The curable material of the present invention may be one composed solely of the fluorinated aromatic compound (A), or it may be a composition which further contains other components in addition to the fluorinated aromatic compound (A).

For example, the curable material of the present invention may, as the case requires, contain a radical polymerization initiator, a conductive agent, a reinforcing material, etc. The conductive agent may, for example, be carbon black such as acetylene black or thermal black, carbon fibers of PAN-type, pitch-type or the like, single-layer or multi-layer carbon nanotubes, graphite, metal fine powder of e.g. silver, copper, nickel or the like, or a metal oxide such as zinc oxide, magnesium oxide or aluminum oxide. Further, the reinforcing material may, for example, be polytetrafluoroethylene, polyvinylidene fluoride, polyvinyl fluoride, polychlorotrifluoroethylene, a TFE/ethylene copolymer, a TFE/propylene copolymer, or a TFE/vinylidene fluoride copolymer. One of these components may be used alone, or two or more of them may be used in combination.

It is also preferred to add the fluorinated aromatic compound (A) of the invention, to a various known thermosetting composition or photocurable composition to obtain a curable material. By containing the fluorinated aromatic compound (A) of the present invention, the curable material will be excellent in curability, and an obtainable cured product will be excellent in optical characteristics such as transparency and mechanical characteristics.

[Cured Product]

A cured product of the present invention is one formed by curing the above curable material.

The curing method is preferably heating (thermal curing), or light irradiation (photo-curing).

The curing condition in the case of thermal curing is preferably from 130° C. to 180° C.

The light to be used for photo-curing is preferably one with a wavelength of from 200 nm to 400 nm.

A specific example of the method for producing a cured product may, for example, be a method wherein a curable material in a solid state (such as a powder) is filled in a mold of an optional shape and heated (thermally cured), or a method wherein a solid dissolved in a solvent is applied on a substrate and then heated (thermally cured) or irradiated with light (photo-cured).

A cured product obtainable by curing the curable material of the present invention will be excellent in transparency, heat resistance, light resistance and mechanical properties.

Thus, the cured product of the present invention is useful as an optical member.

[Optical Member]

The optical member of the present invention is one comprising the cured product of the present invention. The cured product of the present invention may constitute a part or whole of the optical member.

The optical element may, for example, be an optical film, an optical sheet, a transparent substrate, a lens, an adhesive, an optical waveguide, a solar cell component, a light emitting diode (LED), a phototransistor, a photodiode, an optical semiconductor element such as a solid-state image sensor, an illumination device or an image display apparatus. The image display apparatus may, for example, be a plasma display (PDP), a cathode ray tube (CRT), a field emission display (FED), an organic EL display, a 3D display or an electronic paper.

EXAMPLES

Now, the present invention will be described in detail with reference to Examples, but it should be understood that the present invention is by no means limited to these Examples. Here, the respective measurement items were measured by the following methods.

(With Respect to Fluorinated Aromatic Compound and its Cured Product)

[NMR Analyses of Fluorinated Aromatic Compound]

$^1$H NMR spectrum and $^{19}$F NMR spectrum of a fluorinated aromatic compound were measured by means of FT NMR device JNM-AL300, manufactured by JEOL Ltd. (JEOL).

<Thermal Properties>

[Glass Transition Temperature (Tg)]

The glass transition temperature (Tg) of a fluorinated aromatic compound or its cured product was measured by DSC Q-100 manufactured by TA Instrument Co. It was measured under such a condition that the temperature was raised to 135° C. at a heating rate of 10° C./min, then lowered at a cooling rate of 20° C./min, and raised again to 135° C. at a heating rate of 10° C./min, and the temperature at the inflection point of the obtained DSC curve was taken as Tg.

[Melting Point (Tm)]

The melting point (Tm) of a fluorinated aromatic compound or its cured product was measured by DSC Q-100 manufactured by TA Instrument Co. It was measured under such a condition that the temperature was raised to 135° C. at a heating rate of 10° C./min, then lowered at a cooling rate of 20° C./min, and raised again to 135° C. at a heating rate of 10° C./min, and the temperature at the peak top of the endothermic peak of the obtained DSC curve was taken as Tm. Here, in a case where a plurality of Tm were observed, they were presented as $Tm_1$, $Tm_2$, $Tm_3$, etc. from the lower side. The reason as to why a plurality of Tm are observed, is considered to be that a plurality of crystalline states exist.

[Differential Thermal-Thermogravimetric Simultaneous Measurement (TG-DTA)]

The 1% weight reduction temperature ($T_{1d}$) and the 5% weight reduction temperature ($T_{5d}$) of a cured product of a fluorinated aromatic compound were measured by TG-DTA2000SA of NETZSCH. The measurement was made in the presence of air at a temperature-raising rate of 10° C./min, and on the TG curve, the temperature at a weight reduction of 1% was taken as $T_{1d}$, and the temperature at a weight reduction of 5% was taken $T_{5d}$.

<Optical Properties>

[Refractive Index]

The refractive index ($nD^{20}$) of a cured product of a fluorinated aromatic compound was measured by Abbe refractometer NAR-2T manufactured by Atago Co. under conditions of a wavelength of 589.3 nm at a temperature of 20° C. As an intermediate solution, 1-bromonaphthalene was used.

[Hue]

The yellow index (YI) of a cured product of a fluorinated aromatic compound was measured by Colour Cute i, manufactured by Suga Test Instruments Co. This value is a value measured in accordance with the standards of JIS K7373.

<Mechanical Properties>

[Flexural Strength, and Flexural Modulus]

The flexural strength and flexural modulus of a cured product of a fluorinated aromatic compound, were measured by a three-point bending test by means of a small bench testing machine EZ TEST, manufactured by Shimadzu Corp. (With respect to Fluorinated Elastomer Composition and its Crosslinked Product)

[Copolymerization Composition of Fluorinated Elastomer]

With respect to a fluorinated elastomer, the measurement of $^{19}F$-NMR was carried out by FT-NMR apparatus JNM-AL300, manufactured by JEOL Ltd. (JEOL), and from the results thereby obtained, the copolymerization composition was determined.

[Method for Measuring Storage Elastic Modulus G' of Fluorinated Elastomer]

A value measured by using RPA2000 manufactured by Alpha Technologies Inc., and in accordance with ASTM D5289 and D6204, at a temperature of 100° C., at an amplitude of 0.5 degree, at a vibration frequency of 50 times/min, was taken as the storage modulus G'.

[Iodine Atom Content]

2 mg of a fluorinated elastomer was burned and a generated gas was absorbed in a 0.02 mass % hydrazine aqueous solution. The obtained solution was analyzed by an ICP emission method to measure the content of iodine in the solution, and from the obtained results, the content of iodine atoms in the fluorinated elastomer was determined.

[Heat Resistance Test]

A sample (a crosslinked product of a crosslinkable fluorinated elastomer composition having a size of 10 mm×30 mm and a thickness of 1 mm) for a heat resistance test was heated in a hot air oven at a predetermined temperature for a predetermined time and then taken out and visually observed, whereby the heat resistance in the heat resistance test at a predetermined temperature for a predetermined time, was evaluated by the following standards.

○ (good): The sample did not deform.

X (bad): The sample deformed.

The heat resistance test was conducted by starting from the shortest heating time at 300° C. among conditions of 300° C.×48 hours, 300° C.×72 hours, 325° C.×24 hours, 325° C.×48 hours and 325° C.×72 hours, and when the evaluation became "X", no further heat resistance test under a longer time or higher temperature condition was carried out.

[Chemical Resistance Test]

In a sample bottle, a sample (a crosslinked product of a crosslinkable fluorinated elastomer composition having a size of 13 mm×13 mm and a thickness of 1 mm) for a chemical resistance test was immersed in a 48% NaOH aqueous solution and in DMAc, respectively, and maintained at 40° C. for 180 hours, whereupon it was taken out and visually observed to evaluate the chemical resistance by the following standards.

○ (good): None of coloration, swelling and shrinkage was observed in the sample.

X (bad): A change in any of coloration, swelling and shrinkage was observed in the sample.

Synthesis Example 1: Synthesis of Fluorinated Elastomer (F1) with Iodine Terminal Into a stainless steel pressure resistant reactor having an inner volume of 20 L and equipped with an anchor type stirring blade, 8,770 g of degassed ion exchanged water, 733 g of $CF_3CF_2OCF_2CF_2OCF_2COONH_4$, 15.9 g of disodium hydrogen phosphate 12 hydrate and 18.0 g of $CF_2$=CFO$(CF_2)_4OCF$=$CF_2$ (hereinafter referred to as C4DVE) were charged, and the gas phase was replaced with nitrogen. With stirring at a rotational speed of 375 rpm, 554 g of $CF_2$=CFO—$CF_3$ (hereinafter referred to as PMVE) and 115 g of TFE were charged, and the inner temperature was raised up to 80° C. The internal pressure was 0.90 MPaG (G means a gauge pressure). 40 mL of a 2.5 mass % aqueous solution of ammonium persulfate was added to initiate the polymerization.

As the internal pressure of the reactor decreases with the progress of the polymerization, at the time when the internal pressure dropped to 0.89 MPaG, TFE gas was injected to increase the internal pressure to 0.91 MPaG. By repeating this operation, the internal pressure of the reactor was held at from 0.89 to 0.91 MPaG to continue the polymerization reaction. When the added amount of TFE became 30 g, 16.0 g of 1,4-diiodoperfluorobutane was added by nitrogen back pressure. Subsequently, every time when 80 g of TFE had been added, 80.0 g of PMVE was added by nitrogen back pressure. Injection of PMVE was continued until 800 g of TFE was added. The sum of the added amounts of PMVE from the initiation of the polymerization to the end, was 635 g.

When the total added amount of TFE after addition of the aqueous ammonium persulfate solution became 800 g, the addition of TFE was stopped, and the inner temperature of the reactor was cooled to 10° C. to terminate the polymerization reaction. 6,530 g of a latex of the fluorinated elastomer (F1) with iodine terminal, was obtained. The polymerization time was 9 hours. The solid content concentration in the latex was 20 mass %.

While stirring 5,000 g of the latex, 50 g of 96% sulfuric acid was added to the latex to coagulate the fluorinated elastomer (F1). The coagulate was separated and then washed 10 times with 5,000 g ultrapure water each time. By vacuum drying at 50° C. for 12 hours, a white fluorinated elastomer (F1) was obtained.

The copolymerization composition of the fluorinated elastomer (F1) was structural units based on TFE/structural units based on PMVE/structural units based on C4DVE=76/24/0.10 (molar ratio), and no signal based on a polymerizable double bond derived C4DVE was observed. Thus, it is considered that all vinyl groups in C4DVE were consumed during the polymerization, and no vinyl group was present in the fluorinated elastomer (F1).

The content of iodine atoms in the fluorinated elastomer (F1) was 18.8 μmol/g. Further, the storage modulus G' was 495 kPa.

Example 1: Synthesis of Fluorinated Aromatic Compound (A-1)

Into a 2 L four-necked flask equipped with a three-way cock for introducing nitrogen, and a thermocouple thermometer, 82.2 g of perfluorobiphenyl, and 98.4 g of p-acetoxystyrene, were put and dissolved in 708.9 g of DMAc. Then, 140.0 g of a 48% potassium hydroxide aqueous solution was added and stirred for a reaction. The temperature of the reaction solution was controlled within a range of from 8 to 9° C., and the reaction was conducted for 24 hours. Then, the reaction crude liquid was dropped into 3,090 g of 0.5N hydrochloric acid, whereby a white solid precipitated. The obtained solid was collected by filtration and washed twice with ion-exchanged water to obtain 122 g (yield: 92.8%) of the fluorinated aromatic compound (A-1) as white solid.

With respect to the obtained fluorinated aromatic compound (A-1), analyses by NMR and DSC were conducted. The results are shown below.

$^1$H-NMR, $^{19}$F-NMR spectra:

$^1$H-NMR (300.4 MHz, solvent: deuterated acetone, standard: tetramethylsilane (TMS), internal standard: bis(trifluoromethyl) benzene) δ (ppm): 7.55, 7.20, 6.75, 5.80, 5.25.

$^{19}$F-NMR (282.7 MHz, solvent: deuterated acetone, standard: $CFCl_3$, internal standard: bis(trifluoromethyl) benzene) δ (ppm): −140.0, −155.5.

$Tg$=−1.6° C., $Tm_1$=79.5° C., $Tm_2$=107.3° C.

From the above results, the fluorinated aromatic compound (A-1) was confirmed to have the following structure.

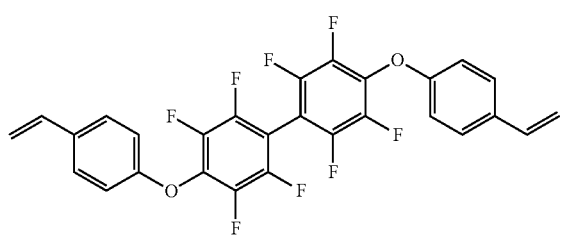

Example 2: Synthesis of Fluorinated Aromatic Compound (A-1)

Into a 200 mL three-necked flask equipped with a three-way cock for introducing nitrogen, and a thermocouple thermometer, 10.0 g of perfluorobiphenyl and 12.2 g of p-acetoxystyrene were put and dissolved in 60 g of diglyme. Then, 20.6 g of a 48% potassium hydroxide aqueous solution was added and stirred for a reaction. The temperature of the reaction solution was controlled at 45° C., and the reaction was conducted for 15 hours. Then, the reaction crude liquid was dropped into 312 g of 0.5N hydrochloric acid, whereby a white solid precipitated. The obtained solid was collected by filtration and washed twice with ion-exchanged water, to obtain 15.1 g (yield: 94.2%) of the fluorinated aromatic compound (A-1) as white solid.

With respect to the obtained fluorinated aromatic compound (A-1), analyses by NMR were conducted, whereby results similar to those in Example 1 were obtained.

$Tg$=0.1° C., $Tm_1$=81.6° C., $Tm_2$=108.9° C. The reason as to why Tg and Tm are different from Example 1 is considered to be error due to the data analysis.

Note that in Example 1 and Example 2, the same fluorinated aromatic compound (A-1) was prepared by changing the solvent and the reaction conditions. Specifically, in Example 1 using DMAc as the solvent, the reaction was carried out at from 8 to 9° C. for 24 hours, and in Example 2 using diglyme as the solvent, the reaction was carried out at 45° C. for 15 hours. This is because when the reaction is carried out in DMAc as a polar solvent, the reaction is likely to proceed easily even at a low temperature as compared with diglyme as a low-polar solvent. However, if the reaction temperature is too high, a side reaction is likely to occur to inhibit the production of the desired product, and therefore, a care should be taken in the selection of the reaction temperature.

Example 3: Synthesis of Fluorinated Aromatic Compound (A-2)

Into a 1 L four-necked flask equipped with a three-way cock for introducing nitrogen, and a thermocouple thermometer, 25.0 g of perfluorotoluene and 68.7 g of p-acetoxystyrene were put and dissolved in 385.0 g of diglyme. Then, 102.5 g of a 48% sodium hydroxide aqueous solution was added and stirred for a reaction. The temperature of the reaction solution was controlled at 60° C., and the reaction was conducted for 6 hours. Then, the reaction crude liquid was dropped into 1,744 g of 0.5N hydrochloric acid, whereby a white solid precipitated. The obtained solid was collected by filtration and washed twice with ion-exchanged water, to obtain 30.1 g (yield: 53.0%) of the fluorinated aromatic compound (A-2) as white solid.

With respect to the obtained fluorinated aromatic compound (A-2), analyses by NMR and DSC were conducted. The results are shown below.

$^1$H-NMR, $^{19}$F-NMR spectra:

$^1$H-NMR (300.4 MHz, solvent: acetone, standard: TMS, internal standard: bis(trifluoromethyl) benzene) δ (ppm): 7.50, 7.15, 6.75, 5.75, 5.20.

$^{19}$F-NMR (282.7 MHz, solvent: deuterated acetone, standard: $CFCl_3$, internal standard: bis(trifluoromethyl) benzene) δ (ppm): −56.7, −142.0.

$Tg$=−0.4° C., $Tm_1$=122.1° C., $Tm_2$=130.2° C.

From the above results, the fluorinated aromatic compound (A-2) was confirmed to have the following structure.

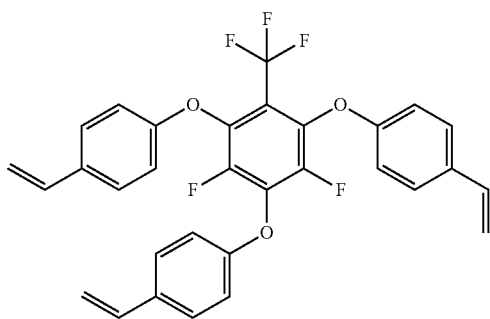

Example 4

920 mg of the fluorinated aromatic compound (A-1) obtained in Example 1 was put in a square box of 10 mm×35 mm×35 mm made of polytetrafluoroethylene (hereinafter referred to as PTFE), and heated at 120° C. for 15 minutes. Then, the temperature was raised and heated at 170° C. for 30 minutes, whereby a cured product (X-1) of 0.7 mm×35 mm×35 mm was obtained.

With respect to the obtained cured product (X-1), the thermal properties, optical properties and mechanical properties were evaluated. The results are shown below.

The glass transition temperature (Tg) and melting point (Tm) of the cured product (X-1): TG and Tm were not observed.

The 1% weight reduction temperature ($T_{1d}$) and 5% weight reduction temperature ($T_{5d}$) of the cured product (X-1): $T_{1d}$ was 336° C., and $T_{5d}$ was 450° C.

The refractive index ($nD^{20}$) of the cured product (X-1): $nD^{20}$ was 1.412.

Yellowness index (YI) of the cured product (X-1): YI was as low as 2.3, and the hue was good.

The flexural strength and flexural modulus of the cured product (X-1): The flexural strength was 22.3 MPa, and the flexural modulus was 1.237 GPa.

Example 5

927 mg of the fluorinated aromatic compound (A-1) obtained in Example 2 was put in a PTFE square box of 10 mm×35 mm×35 mm and heated at 120° C. for 15 minutes. Then, the temperature was raised and heated at 170° C. for 30 minutes, whereby a cured product (X-2) of 0.7 mm×35 mm×35 mm was obtained.

With respect to the obtained cured product (X-2), the thermal properties, optical properties and mechanical properties were evaluated. The results are shown below.

The glass transition temperature (Tg) and the melting point (Tm) of the cured product (X-2): Tg and Tm were not observed.

The 1% weight reduction temperature ($T_{1d}$) and 5% weight reduction temperature ($T_{5d}$) of the cured product (X-2): $T_{1d}$ was 338° C., and $T_{5d}$ was 451° C.

The refractive index ($nD^{20}$) of the cured product (X-2): $nD^{20}$ was 1.407.

Yellowness index (YI) of the cured product (X-2): YI was as low as 2.1, and the hue was good.

The flexural strength and flexural modulus of the cured product (X-2): The flexural strength was 24.6 MPa, and the flexural modulus was 1.382 GPa.

Example 6

920 mg of the fluorinated aromatic compound (A-2) was put in a PTFE square box of 10 mm×35 mm×35 mm and heated at 170° C. for 30 minutes, whereby a cured product of 0.7 mm×35 mm×35 mm (X-3) was obtained.

With respect to the obtained cured product (X-3), the thermal properties, optical properties and mechanical properties were evaluated. The results are shown below.

Tg and Tm of the cured product (X-3) were not observed.

The 1% weight reduction temperature ($T_{1d}$) and 5% weight reduction temperature ($T_{5d}$) of the cured product (X-3): $T_{1d}$ was 412° C., and $T_{5d}$ was 465° C.

The refractive index ($nD^{20}$) of the cured product (X-3): $nD^{20}$ was 1.408.

Yellowness index (YI) of the cured product (X-3): YI was as low as 2.1, and the hue was good.

The flexural strength and flexural modulus of the cured product (X-3): The flexural strength was 44.8 MPa, and the flexural modulus was 1.898 GPa.

Example 7: Synthesis of Fluorinated Aromatic Compound (A-2)

Into a 1 L four-necked flask equipped with a three-way cock for introducing nitrogen and a thermocouple thermometer, 20.1 g of perfluorotoluene and 51.4 g of p-acetoxystyrene were put and dissolved in 143.3 g of diglyme. Then, 73.4 g of a 48% sodium hydroxide aqueous solution was added and stirred for a reaction. The temperature of the reaction solution was controlled at 45° C., and the reaction was conducted for 15 hours. Then, the reaction crude liquid was dropped in 497.7 g of 0.1 N hydrochloric acid, whereby a white solid precipitated. The obtained solid was collected by filtration and washed twice with ion-exchanged water, to obtain 39.4 g (yield: 86.0%) of the fluorinated aromatic compound (A-2) as white solid.

With respect to the obtained fluorinated aromatic compound (A-2), analyses by NMR were conducted, whereby results similar to those in Example 3 were obtained.

Tg=−0.1° C., $Tm_1$=122.7° C., $Tm_2$=130.6° C. The reason as to why Tg and Tm are different from Example 3 is considered to be error due to the data analysis.

The results in Examples 4 to 6 are summarized in Table 1.

TABLE 1

| | | Example 4 | Example 5 | Example 6 |
|---|---|---|---|---|
| Fluorinated aromatic compound | | (A-1) | (A-1) | (A-2) |
| Tg (° C.) of fluorinated aromatic compound | | −1.6 | 0.6 | −0.4 |
| Tm (° C.) of fluorinated aromatic compound | | 79.5, 107.3 | 81.6, 108.9 | 122.1, 130.2 |
| Cured product | | (X-1) | (X-2) | (X-3) |
| Thermal properties of cured product | Tg (° C.) | Not observed | Not observed | Not observed |
| | Tm (° C.) | Not observed | Not observed | Not observed |
| | $T_{1d}$ (° C.) | 336 | 338 | 412 |
| | $T_{5d}$ (° C.) | 450 | 451 | 465 |
| Optical properties of cured product | $nD^{20}$ | 1.412 | 1.407 | 1.408 |
| | YI | 2.3 | 2.1 | 2.1 |
| Mechanical properties of cured product | Flexural strength (MPa) | 22.3 | 24.6 | 44.8 |
| | Flexural modulus (GPa) | 1.237 | 1.382 | 1.898 |

If the 1% weight reduction temperature ($T_{1d}$) is at least 300° C. and the 5% weight reduction temperature ($T_{5d}$) is at least 400° C., it is judged to have a sufficient heat resistance for optical applications.

Further, if YI is at most 5, it is judged to have sufficiently low yellowness for optical applications.

If the flexural strength is from 10 to 200 MPa, and the flexural modulus is from 0.5 to 5.0 GPa, it is judged to have sufficient mechanical properties for optical applications.

In the cured products in Examples 4 to 6, no melting point (Tm) was observed, and they did not flow even when heated to 300° C., whereby it was confirmed that the fluorinated aromatic compound (A-1) and the fluorinated aromatic compound (A-2) were sufficiently cured, respectively.

Further, from the measurement results of the thermal properties, optical properties and mechanical properties, it was confirmed that each of the cured products in Examples 4 to 6 had excellent heat resistance, optical properties and mechanical properties.

Reference Example A 1.01 g of the fluorinated elastomer (F1), 0.104 g of the fluorinated aromatic compound (A-1) obtained in Example 1, 20.0 g of 1H-tridecafluoro-hexane (AC-2000 manufactured by Asahi Glass Company, Limited; hereinafter referred to as AC-2000), 0.0306 g of magnesium oxide, and 0.0203 g of 2,5-dimethyl-2,5-di(t-butylperoxy) hexane (Perhexa 25B manufactured by NOF Corporation; hereinafter referred to as Perhexa 25B) were mixed and stirred in a 50 mL egg-plant flask to obtain a dispersion of a crosslinkable fluorinated elastomer composition.

The dispersion was cast onto a PTFE sheet, and the solvent was removed by nitrogen flow, followed by heat pressing at 170° C. for 12 minutes between stainless steel plates, to obtain a film having a thickness of 1 mm (a crosslinked product of the crosslinkable fluorinated elastomer composition).

The obtained film was cut in 10 mm×30 mm to prepare a sample for a heat resistance test, and a heat resistance test was carried out at a temperature and time shown in Table 1. The results are shown in Table 1.

Further, the obtained film was cut in 13 mm×13 mm to prepare a sample for a chemical resistance test, and a chemical resistant test was carried out. The results are shown in Table 2.

Reference Example B

A dispersion of a crosslinkable fluorinated elastomer composition was prepared in the same manner as in Reference Example A, except that magnesium oxide was not blended, a film having a thickness of 1 mm was prepared, samples for a heat resistance test and a chemical resistance test were prepared from the film, and a heat resistance test and a chemical resistance test were carried out. The results are shown in Table 2.

Reference Example C

A dispersion of a crosslinkable fluorinated elastomer composition was prepared in the same manner as in Reference Example A, except that 1.01 g of the fluorinated elastomer (F1), 0.105 g of the fluorinated aromatic compound (A-2), 20.3 g of AC-2000, 0.0318 g of magnesium oxide, and 0.0165 g of Perhexa 25B were used, a film having a thickness of 1 mm was prepared, samples for a heat resistance test and a chemical resistance test were prepared from the film, and a heat resistance test and a chemical resistance test were carried out. The results are shown in Table 2.

Reference Example D

A dispersion of a crosslinkable fluorinated elastomer composition was prepared in the same manner as in Reference Example C, except that magnesium oxide was not blended, a film having a thickness of 1 mm was prepared, samples for a heat resistance test and a chemical resistance test were prepared from the film, and a heat resistance test and a chemical resistance test were carried out. The results are shown in Table 2.

Comparative Reference Example E

A dispersion of a crosslinkable fluorinated elastomer composition was prepared in the same manner as in Reference Example A, except that 1.02 g of the crosslinkable fluorinated elastomer (F1), 0.104 g of triallyl isocyanurate (hereinafter referred to as TAIC), 20.2 g of AC-2000, 0.0298 g of magnesium oxide, and 0.0180 g of Perhexa 25B were used, a film having a thickness of 1 mm was prepared, samples for a heat resistance test and a chemical resistance test were prepared from the film, and a heat resistance test and a chemical resistance test were carried out. The results are shown in Table 2.

Comparative Reference Example F

A dispersion of a crosslinkable fluorinated elastomer composition was prepared in the same manner as in Reference Example A, except that 1.00 g of the crosslinkable fluorinated elastomer (F1), 0.104 g of 1,6-divinyl perfluorohexane, 20.6 g of AC-2000, 0.0310 g of magnesium oxide, and 0.0185 g of Perhexa 25B were used, a film having a thickness of 1 mm was prepared, samples for a heat resistance test and a chemical resistance test were prepared from the film, and a heat resistance test and a chemical resistance test were carried out. The results are shown in Table 2.

TABLE 2

| | | Reference Examples | | | | Comparative Reference Examples | |
|---|---|---|---|---|---|---|---|
| | | A | B | C | D | E | F |
| Heat resistance | 300° C. × 48 hr | ◯ | ◯ | ◯ | ◯ | ◯ | ◯ |
| | 300° C. × 72 hr | ◯ | ◯ | ◯ | ◯ | X | ◯ |
| | 325° C. × 24 hr | ◯ | ◯ | X | X | — | X |
| | 325° C. × 48 hr | ◯ | ◯ | — | — | — | — |
| | 325° C. × 72 hr | ◯ | X | — | — | — | — |
| Chemical resistance | 48% NaOH aqueous solution | ◯ | ◯ | ◯ | ◯ | ◯ | ◯ |
| | DMAc | ◯ | ◯ | ◯ | ◯ | ◯ | X |

The crosslinked products of the crosslinkable fluorinable elastomer compositions in Reference Examples A to D, showed no deformation at all in the heat resistance test at 300° C. for 72 hours, and thus were excellent in heat resistance. Especially, the crosslinked products of the crosslinkable fluorinated elastomer compositions in Reference Examples A to B, showed no deformation at all even in the heat resistance test at 325° C. for 48 hours.

Further, the crosslinked products of the crosslinkable fluorinated elastomer compositions in Reference Example A to D, showed no coloration, swelling or shrinkage in the chemical resistance test using a 48% NaOH aqueous solution or DMAc, and thus were excellent in chemical resistance.

On the other hand, in the crosslinked product of the crosslinkable fluorinated elastomer composition in Comparative Reference Example E wherein TAIC was used in place of the fluorinated aromatic compound, a large deformation was observed in the heat resistance test at 300° C. for 72 hours, and thus, it was poor in heat resistance.

Further, the crosslinked product of the crosslinkable fluorinated elastomer composition in Comparative Reference Example F wherein 1,6-divinylperfluorohexane was used in place of the fluorinated aromatic compound, was soluble in DMAc, and the volume was contracted. Thus, this crosslinked product was found to be inferior in chemical resistance.

INDUSTRIAL APPLICABILITY

A curable resin obtainable by heating or photocuring the fluorinated aromatic compound of the present invention is useful as an optical member. The optical member may, for example, be an optical film, an optical sheet, a transparent substrate, a lens, an adhesive, an optical waveguide, a solar cell element, a light emitting diode (LED), a phototransistor, a photodiode, an optical semiconductor element such as a solid-state imaging device, an illumination device or an image display device.

Further, the fluorinated aromatic compound of the present invention is useful as a crosslinking aid for a fluorinated elastomer.

Further, the fluorinated aromatic compound of the present invention may be blended in various thermosetting compositions or photocurable compositions and thus used as a modifier for improving the optical characteristics and mechanical properties of the cured products obtained therefrom.

This application is a continuation of PCT Application No. PCT/JP2014/070491, filed on Aug. 4, 2014, which is based upon and claims the benefit of priority from Japanese Patent Application No. 2013-164619 filed on Aug. 7, 2013. The contents of those applications are incorporated herein by reference in their entireties.

What is claimed is:

1. A fluorinated aromatic compound represented by formula (A):

(A)

wherein
n is an integer of from 0 to 6,
a is an integer of from 0 to 5,
b is an integer of from 0 to 4,
c is 0, or c is an integer of from 1 to 4 and $Rf^1$ is a $C_{1-8}$ perfluoroalkyl group,
a+c+n is from 2 to 6,
a+b is from 2 to 9,
Z is a single bond, —O—, —S—, —CO—, —C(CH$_3$)$_2$—, —C(CF$_3$)$_2$—, —SO— or —SO$_2$—,
each of $Y^1$ and $Y^2$ which are independent of each other, is a group represented by formula (1), and F in the aromatic ring represents that hydrogen atoms of the aromatic ring are all substituted by fluorine atoms:

(1)

wherein
s is 0 or 1, and
each of $R^1$, $R^2$, $R^3$ and $R^4$ is a hydrogen atom.

2. The fluorinated aromatic compound according to claim 1, which has a molecular weight of from 300 to 2,000.

3. The fluorinated aromatic compound according to claim 1, represented by formula (A-1) or (A-2):

(A-1)

(A-2)

4. A method for producing the fluorinated aromatic compound according to claim 1, the method comprising:
subjecting an aromatic compound represented by formula (a1) and a fluorinated aromatic compound represented by formula (a2) to a condensation reaction in the presence of a HF elimination agent:

(a1)

(a2)

where
in the formula (a1),
s is 0 or 1,
each of $R^1$, $R^2$, $R^3$ and $R^4$ is a hydrogen atom, and
X is a hydrogen atom, CH$_3$CO, CH$_3$CH$_2$CO, (CH$_3$)$_3$C (CH$_3$)$_2$Si or (CH$_3$)$_3$Si; and
in the formula (a2),
n is an integer of from 0 to 6,
c is 0, or c is an integer of from 1 to 4 and $Rf^1$ is a $C_{1-8}$ perfluoroalkyl group, c+n is from 0 to 6, Z is a single bond, —O—, —S—, —CO—, —C(CH$_3$)$_2$—, —C(CF$_3$)$_2$—, —SO—, or —SO$_2$—, and F in the aromatic ring represents that hydrogen atoms of the aromatic ring are all substituted by fluorine atoms.

5. The method according to claim 4, wherein the aromatic compound represented by the formula (a1) is 4-ethenyl phenol or 4-ethenyl-1-acetoxy benzene.

6. The method according to claim 4, wherein the fluorinated aromatic compound represented by the formula (a2) is perfluorobenzene, perfluorotoluene, perfluoroxylene, perfluorobiphenyl, perfluoroterphenyl, a perfluorotriphenyl benzene, a perfluorotetraphenyl benzene, a perfluoropentaphenyl benzene, a perfluorohexaphenyl benzene, a 1,1'-oxybis[2,3,4,5,6-pentafluorobenzene], a 1,1'-thiobis[2,3,4,5,6-pentafluorobenzene], a bis(2,3,4,5,6-pentafluorophenyl) methanone, a 1,1'-sulfonyl bis[2,3,4,5,6-pentafluoro benzene], or a 1,2,3,4,5-pentafluoro-6-[(2,3,4,5,6-pentafluorophenyl) sulfinyl] benzene.

7. The method for according to claim 4, wherein the HF elimination agent is an alkali metal hydroxide.

8. A curable material, comprising:
the fluorinated aromatic compound according to claim 1.

* * * * *